United States Patent [19]

Aichlmayr et al.

[11] Patent Number: 4,981,476
[45] Date of Patent: Jan. 1, 1991

[54] NEEDLE SAFETY DEVICE

[75] Inventors: James L. Aichlmayr, Aloha, Oreg.; Dallas C. Enslow, Garden City, Kans.

[73] Assignee: Enslow, Inc., Garden City, Kans.

[21] Appl. No.: 278,901

[22] Filed: Dec. 2, 1988

[51] Int. Cl.$^5$ ............................................. A61M 5/32
[52] U.S. Cl. ..................... 604/192; 604/263; 206/365
[58] Field of Search ............. 604/192, 263, 110; 206/369, 365; 24/707.4

[56] References Cited

U.S. PATENT DOCUMENTS

| | | |
|---|---|---|
| 455,392 | 7/1891 | Ellis . |
| 1,061,076 | 5/1913 | Hilditich ........................... 24/707.4 |
| 1,193,111 | 8/1916 | Breidenbach ..................... 24/707.4 |
| 2,854,976 | 10/1958 | Heydrich . |
| 2,930,570 | 3/1960 | Leedy . |
| 3,847,370 | 11/1974 | Engelsher . |
| 3,904,033 | 9/1975 | Haerr . |
| 4,737,149 | 4/1988 | Gillilan ............................. 604/192 |
| 4,781,697 | 11/1988 | Slaughter .......................... 604/192 |
| 4,840,618 | 6/1989 | Marvel .............................. 604/187 |
| 4,850,976 | 7/1989 | Heinrich et al. ................. 604/192 |
| 4,892,525 | 1/1990 | Hermann et al. ................. 604/263 |

FOREIGN PATENT DOCUMENTS

| | | | |
|---|---|---|---|
| 0295888 | 12/1988 | European Pat. Off. ........... 604/263 |
| 437142 | 4/1912 | France ............................. 24/707.4 |
| 2586566 | 3/1987 | France ............................. 604/192 |
| 2586568 | 3/1987 | France ............................. 604/263 |
| 2198644 | 6/1988 | United Kingdom .............. 604/192 |

OTHER PUBLICATIONS

"SAF-T-CAP" Needle cap Holder Sales Brochure, published May, 1988 by B and E Medical Systems, Portland, Ore.

Primary Examiner—C. Fred Rosenbaum
Assistant Examiner—Mark O. Polutta
Attorney, Agent, or Firm—Marger Johnson McCollom & Stolowitz, Inc.

[57] ABSTRACT

A compact, autoclavable needle safety device includes an adjustable cavity having an open position sized to receive a needle protective cap and a closed position to grip the cap within the cavity. The cavity is biased toward one of the positions and adjustable to the other position by single-handed actuation of a handle. In the closed position, the cap is gripped in place while allowing withdrawal of a syringe including a needle for use. The device maintains the cap open-end-up on an underlying surface for reinserting the needle to avoid exposing the user's hand to needle stick injury.

6 Claims, 1 Drawing Sheet

NEEDLE SAFETY DEVICE

BACKGROUND OF THE INVENTION

Needle safety has long been a concern of doctors, dentists and other health professionals. The recent spread of Acquired Immune Deficiency Syndrome (AIDS) has changed a needle prick from a minor irritation to a potentially fatal injury. A July 30, 1988 update from the Surveillance, Forecasting and Impact Assessment Unit of the Global Programs on AIDS reports:

"Since June, 1988, a total of 7,766 AIDS cases have been reported to WHO [World Health Organization], bringing the cumulative world total to 108,176. A total of 177 countries are now reporting to WHO with 140 reporting one or more AIDS cases. About half of this month's increase was reported from the U.S.A. and updated reports from several African countries accounted for most of the other half."

The U.S. Center for Disease Control statistics dated Sept. 5, 1988 show a total of 22,242 AIDS cases reported since Jan. 1, 1988 and a cumulative total of 72,645 cases. These alarming statistics dictate the use of improved safety devices and procedures for anyone potentially exposed to AIDS. Regarding health professionals in particular, the CDC report included one health care worker who developed AIDS after a documented needle stick.

Medical needles generally are covered by a protective cap when not in use. When a needle is so covered, it presents little or no danger of needle stick to a user. A danger is presented when handling an uncapped needle and particularly in the process of recapping a needle. One method of avoiding injury when recapping a needle is to use a needle cap holder to hold the cap during the reinsertion.

A device for holding a syringe including a needle having a protective cap mounted on the syringe is known which includes an enlarged flat base for maintaining the device upright on an underlying surface. It further includes a central elongate well extending into the device and having a longitudinal axis normal to the base for receiving the needle cap and maintaining the syringe upright. The well is internally threaded to hold the cap in place while allowing withdrawal of the needle for use.

Use of such a threaded well device thus requires a user to rotate the syringe in order to engage the cap in the holder. As the cap is free to rotate around the needle, it may be necessary to use both hands to engage the cap in the holder; one hand to support the syringe upright and the other hand to directly rotate the cap to threadably engage it in the holder. This process is cumbersome and time-consuming. For those reasons, a health worker may be discouraged from using the device consistently and instead may take unnecessary risks by handling the needle cap without such a device. Another drawback of the device described is that the syringe is held upright between uses; a display that is disconcerting for many patients.

In the absence of a suitable cap holder, a user simply holds the syringe in one hand and the cap in the other to reinsert the needle in the cap. That procedure obviously is fraught with danger of incurring a needle stick, with the attendant risk of transmitting AIDS, hepatitis, or other blood-borne diseases to the health worker.

A pick guard for shielding the delicate tip of a medical pick or the like is shown in U.S. Pat. No. 3,904,333. That device includes a pair of elongate jaws integrally hinged together at one of their ends for pivotal movement between open and closed positions. It must be held in one hand while the needle is introduced between the jaws and then clamped to a closed position in which it grips the needle. Such a device does not appear suitable for covering the tip of a needle. Its use requires holding the guard in one hand while introducing the needle between the jaws. A miscalculation in that regard likely would lead to a needle stick injury, as no means is provided for shielding a user from such an injury.

A protective device for needles of hypodermic syringes is shown in U.S. Pat. No. 2,854,976. That device is adapted to hold a needle which is separate from the syringe; it is of no benefit for holding a syringe including a needle having a cap mounted thereon or for holding the cap.

Accordingly, the need remains for a needle safety device for protecting a user from needle stick injury while handling a syringe including a needle having a protective cap mounted on the syringe.

SUMMARY OF THE INVENTION

An object of the present invention is to provide a needle safety device to protect a user from needle stick injury. Another object of the invention is to provide for gripping a needle protective cap while allowing withdrawal of the syringe and needle from the cap for use and allowing reinsertion of the needle into the cap after use, while protecting a user from needle stick injury.

A further object of the invention is to provide means for holding a cap in a convenient position for receiving the needle after use, while minimizing risk of needle stick injury to a user when reinserting the needle into the cap.

A needle safety device according to the invention is adapted for use in combination with a syringe including a needle having a disengageable protective cap mounted thereon. The safety device is adapted to receive the needle protective cap and grip the cap in place, while allowing withdrawal of the needle for use and allowing reinsertion of the needle after use.

The device is formed of a generally U-shape strip of a resilient sheet material, preferably metal, including a pair of oppositely disposed resilient flexible legs. A terminal portion of a first one of the legs extends toward the second leg to form a flat front plate. The front plate includes a first aperture sized for receiving the cap and includes a flange extending outward around the first aperture to shield a user's fingers during reinsertion of the needle into the cap. A lip extends around the periphery of the flange to limit the needle from slipping off the flange during reinsertion into the cap.

A terminal portion of the second leg extends toward the first leg, overlapping and behind the front plate, to form a back plate. The back plate includes a second aperture also sized for receiving the cap. The front and back plates are approximately parallel to each other.

The front plate and the back plate are laterally movable with respect to each other by moving the legs. The apertures in the front and back plates provide in combination an adjustable cavity. The first aperture defines an open end of the cavity for receiving the cap. The cavity has an open position—when the two plate apertures are registered with each other, and a closed position—when the plate apertures are offset. In the preferred embodiment, the first and second apertures are biased toward a position axially offset from each other. In an alternative embodiment, the apertures are normally aligned or registered with each other.

In the preferred embodiment, moving the legs together registers the plate apertures to adjust the cavity to the open position for receiving the cap. When released, the legs return to offset the plate apertures thereby adjusting the cavity to the closed position. In an alternative embodiment, the plate apertures normally are registered, and the legs are moved together to offset them for adjusting the cavity to the closed or grip position.

Another aspect of the invention is a method of using a syringe including a needle having a disengageable protective cap mounted thereon, the method comprising the steps of providing a needle safety device including a cavity having an open end and further including means for adjusting the size of the cavity; inserting the cap through the open end into the cavity; adjusting the size of the cavity to grip the cap; withdrawing the needle from the cap and safety device for use; reinserting the needle into the cap after use; adjusting the size of the cavity to release the cap; and removing the cap and needle from the safety device.

The cavity size adjusting means may be biased toward a position in which the size of the cavity is smaller than the size of the cap, in which case the step of inserting the cap includes moving the adjusting means to a position in which the size of the cavity is greater than the size of the cap. Alternatively, where the aperture is biased toward the open position and the safety device includes a handle for adjusting the aperture, said adjusting the aperture to the closed position includes actuating the handle means.

The foregoing and other objects, features and advantages of the invention will become more readily apparent from the following detailed description of a preferred embodiment which proceeds with reference to the drawings.

DETAILED DESCRIPTION OF A PREFERRED EMBODIMENT

Figure 1:
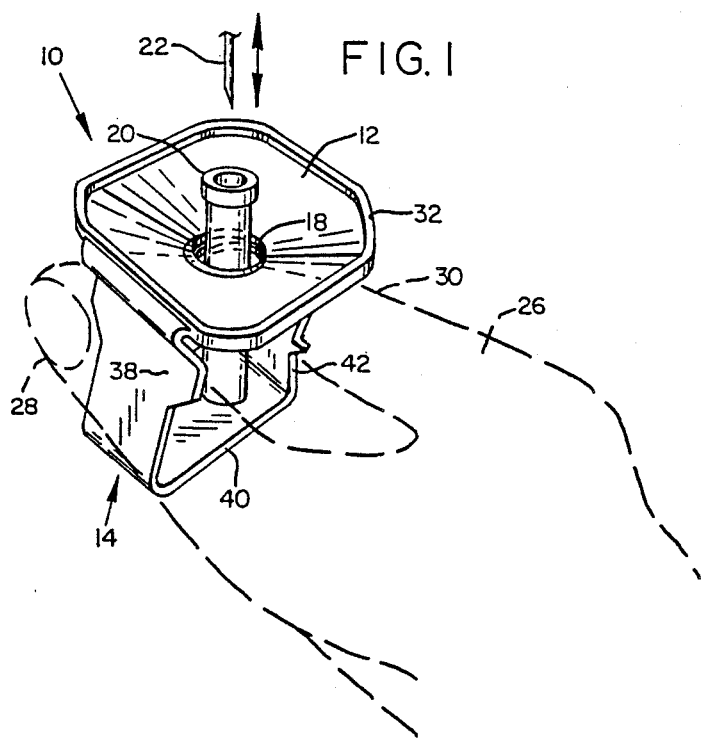
FIG. 1 is a perspective view of a needle safety device according to the present invention showing a protective cap extending into a cavity in the device and a needle being withdrawn from the protective cap. A user's hand, holding the safety device, is shown in phantom.

FIG. 1 shows a needle safety device 10 according to the present invention. The safety device 10 generally comprises a front plate 12 connected to a handle 14. The front plate 12 includes a central aperture 18 for receiving a needle cap 20. Aperture 18 should be sized slightly larger than the diameter of cap 20 for inserting and withdrawing the cap from the device; yet aperture 18 should be sized only slightly larger than cap 20 for gripping the cap in the device as more fully explained below.

The front plate 12 may be generally planar, although preferably, it is tapered downwardly toward the handle 14 in a central area surrounding aperture 18 to form a funnel shape to help guide cap 20 into the aperture. Front plate 12 includes an upstanding lip 32 extending around the periphery of the front plate 12. Lip 32 helps to limit a needle 22 from slipping off the front plate 12 in the event a user misses the cap while attempting to reinsert a needle 22 into the cap 20.

Figure 3:
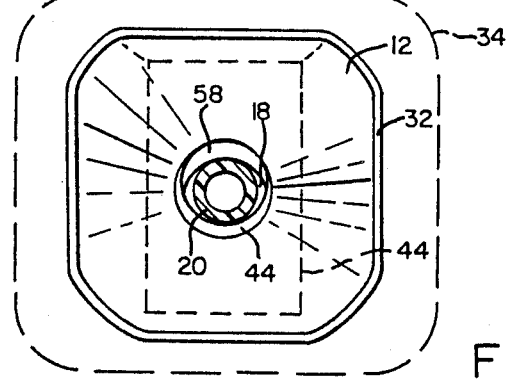
FIG. 3 is a top view of the needle safety device of FIG. 1 showing an alternative configuration of a shield flange in phantom.

Referring to FIG. 3, the front plate 12 may include an enlarged flange indicated by dashed line 34 to provide enhanced safety by shielding a portion of a user's hand 26 (FIG. 1) so that, in the event a needle 22 misses the cap 20, it will strike the plate 12 or flange 34 rather than the user's hand. The outline configuration of front plate 12 is not critical and any convenient configuration, such as a square or circle, may be used.

Figure 2:
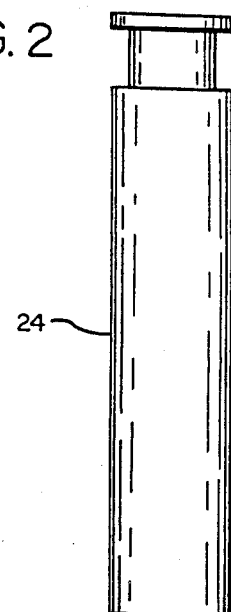
FIG. 2 is a side elevational view of the safety device of FIG. 1, the user's fingers squeezing the legs together to open the cavity to receive or release a syringe including a needle having a disengageable protective cap mounted thereon, the needle and cap engaged in the safety device.

Referring now to FIG. 2, needle safety device 10 is formed of a generally U-shape strip of a resilient sheet material including a pair of oppositely disposed resilient flexible legs 38,42. The legs include indentations 48,52 respectively to accommodate a user's fingers 28,30 to facilitate handling the device and to limit the position of a cap gripped in the device as described below. The strip also includes a flat base portion 40 intermediate the legs 38,42 for maintaining the device upright on an underlying surface.

Figures 4, 5:
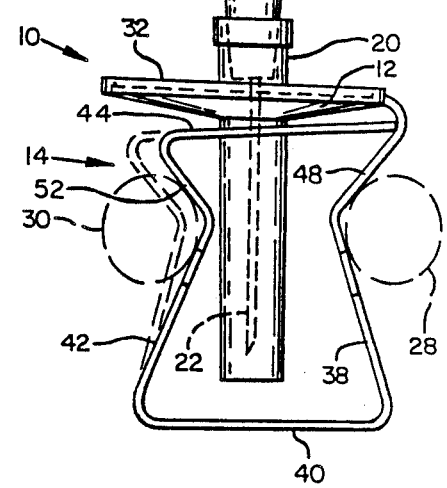
FIG. 4 is a side elevational view of the safety device of FIG. 1 with the cap removed.
FIG. 5 is a cross-sectional view taken along line 5—5 of FIG. 4 additionally showing a cap engaged in the safety device and a needle aligned with the cap for reinsertion into the cap.
Figure 6:
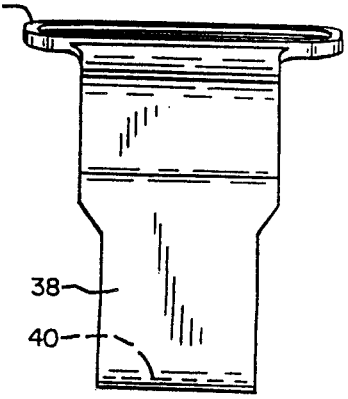
FIG. 6 is a side elevational view opposite to the view of FIG. 4 of the needle safety device of FIG. 1 with the cap removed.

A terminal portion of leg 38 extends toward the second leg 42 to form front plate 12. A terminal portion of the second leg 42 extends toward the first leg 38, overlapping and behind the front plate 12, to form a back plate 44. Back plate 44 includes a second aperture 46 (FIG. 4) having a diameter approximately the same as that of aperture 18.

Device 10 thus includes an adjustable cavity having an open end defined by aperture 18. The cavity is adjustable by moving legs 38, 42 between an open position and a closed position. It is in an open position for receiving or releasing cap 20 when apertures 18 and 46 are registered with each other. The cavity is in a closed position for gripping the cap when apertures 18 and 46 are offset or misaligned. In the open position, the cavity has a cross-sectional size approximately equal to the diameter of aperture. In the closed position, the effective cross-sectional size of the cavity is diminished, as best seen in FIG. 3. The resting or unbiased relationship of the legs is shown in phantom in FIG. 2. When the legs are in the rest position, the apertures 18,46 are offset from each other so that the device is closed, as further described below. In an alternative embodiment, apertures 18,46 normally are registered.

Front plate 12 and back plate 44 are movable with respect to each other by squeezing the legs 38,42 toward each other. Squeezing the legs together registers apertures 18,46 with each other to open the device for receiving or releasing cap 20, as shown in FIG. 2. When the apertures are fully aligned or registered, the end of the strip that forms back plate 44 contacts the interior of leg 38 adjacent front plate 12, thereby preventing further movement of the legs toward each other. This enables a user to simply squeeze the device to open it, without having to visually confirm that the device is open. Further, if overshoot of the legs were allowed, it would of course offset the apertures from each other and thereby undesirably close the device.

A syringe 24 including a cap 20 is inserted into the device through aperture 18 while it is open, as in FIG. 1. When released, the legs move toward the unbiased or closed position. The opposing movement of front plate 12 and back plate 44 pulls cap 20 toward leg 42. The cap abuts leg 42 at a position 50, thereby preventing the device from completely returning to the closed position, illustrated by dashed lines in FIG. 5. The cap thus is gripped in the device, as seen in top view in FIG. 3, while allowing the syringe and needle to be withdrawn from the cap. The device holds the cap in the position shown, so that, when the device is positioned with base 40 resting on an underlying surface such as a table, the cap is maintained in a convenient position for reinserting the needle 22 into the cap.

To enhance the grip on cap 20, front plate 12 is countersunk along a peripheral edge 58 of the first aperture 18, as shown in FIG. 3, to form a sharp edge for engaging cap 20, as the cap conventionally is made of a resilient material, for example, a polymeric material. An edge of aperture 46 may similarly be sharpened for the same purpose.

Preferably, the entire safety device including the base portion 40, legs 38, 42, front plate 12 and back plate 44 are integrally formed of a strip of resilient material. The resilient material preferably is a metal, for example stainless steel, so that the device is autoclavable.

The protective device 10 is used as follows. To begin, a user obtains a syringe containing medicine to be administered and including a needle having a disengageable protective cap mounted thereon. The user holds the syringe 24 in one hand and the protective device 10 in the other. The user then squeezes the legs of the protective device together to adjust the cavity to the open position, and while it is open, axially inserts the cap through aperture 18 into the cavity. The user then relaxes the legs, thereby adjusting the cavity to the closed position to grip the cap.

The combined safety device and syringe may be placed prone on an underlying surface such as a table top, preferably near the patient, until the syringe is needed. Flat sides of the front plate 12 or enlarged flange 34 prevent the combination from rolling off the table. In such a prone position, the syringe and needle are unlikely to be noticed by the patient, particularly if the table has a raised lip along its perimeter that obscures a view of the table top.

When the syringe is needed, the user withdraws the needle from the cap and safety device for use. Preferably, the user then places the safety device on the table so that base 40 supports the protective device upright, thereby maintaining the cap open side up for later receiving the needle.

After using the syringe, the user reinserts the needle into the cap. This requires the use of only one hand, the hand holding the syringe, if the protective device holds the cap ready as noted. In this way, the user's other hand may be kept away from the bare needle in order to minimize the risk of a needle stick injury. Alternatively, some users may prefer to hold the safety device in one hand while reinserting the needle with the other. In that event, a portion of the one hand is protected by the front plate and extended flange to reduce the risk of needle stick injury. To do so, the user need merely hold the safety device containing the cap in one hand, hold the syringe in the other hand, and reinsert the needle into the cap.

After the needle is securely engaged in the cap, the user squeezes the legs together as described above to adjust the cavity to the open position to release the cap and removes the syringe along with the needle having the protective cap mounted thereon from the safety device.

A health professional, for example, a dentist, may have occasion to administer medicine repeatedly to the same patient during a single procedure. Under such circumstances, it is unnecessary to change needles. During such a procedure, the safety device 10 conveniently holds the protective cap in an upright position by resting the safety device on an underlying surface, so that the user can reinsert the needle into the cap between uses. At such times, after reinserting the needle, it is preferable to rest the syringe and safety device combination prone on the underlying surface, so that the syringe and needle are not displayed in view of the patient. This is advantageous, as many patients find the sight of a syringe and needle disconcerting.

Having illustrated and described the principles of our invention in a preferred embodiment thereof, it should be readily apparent to those skilled in the art that the invention can be modified in arrangement and detail without departing from such principles. We claim all modifications coming within the spirit and scope of the accompanying claims.

We claim:

1. A needle safety device for use in combination with a syringe including a needle having a disengageable protective cap mounted thereon, the device comprising:
   a generally U-shape strip of a resilient sheet material including a pair of oppositely disposed resilient flexible legs and a flat base region intermediate the legs;
   a terminal portion of a first one of the legs extending toward the second leg to form a flat front plate substantially parallel to the base region, the front plate including means defining a first aperture sized for receiving the cap and the front plate including a flange extending outward around the first aperture to shield a user's fingers during reinsertion of the needle into the cap;
   a terminal portion of the second leg extending toward the first leg overlapping and behind the front plate to form a back plate substantially parallel to the front plate, the back plate including means defining a second aperture sized for receiving the cap, the second aperture being offset from the first aperture;
   the legs being arranged to register the first and second apertures with each other responsive to squeezing the legs toward each other thereby forming a cavity for receiving the cap.

2. A device according to claim 1 wherein the front plate includes a peripheral lip to limit the needle tip from slipping off the front plate during reinsertion of the needle into the cap.

3. A device according to claim 1 wherein the front plate is countersunk along a peripheral edge of the first aperture means so as to form a sharp edge to facilitate gripping the cap in the device.

4. A device according to claim 1 wherein the legs each include a flat edge for maintaining the device and the syringe prone on an underlying surface.

5. A device according to claim 1 wherein the U-shape strip includes a flat base portion intermediate the legs and parallel to the front plate for maintaining the device upright on an underlying surface.

6. A needle safety device for use in combination with a syringe including a needle having a disengageable protective cap mounted thereon, the device consisting of:

a generally U-shape strip of a resilient sheet material, formed to define a pair of oppositely disposed resilient flexible legs and a flat base region intermediate the legs;

a terminal portion of a first one of the legs extending toward the second leg to form a flat front plate substantially parallel to the base region, the front plate including means defining a first aperture sized for receiving the cap and the front plate including a flange extending outward around the first aperture to shield a user's fingers during reinsertion of the needle into the cap;

a terminal portion of the second leg extending toward the first leg overlapping and behind the front plate to form a back plate substantially parallel to the front plate, the back plate including means defining a second aperture sized for receiving the cap, the second aperture being offset from the first aperture;

the legs being arranged to register the first and second apertures with each other responsive to squeezing the legs toward each other thereby forming a cavity for receiving the cap.

* * * * *